United States Patent [19]

Rudo

[11] Patent Number: 5,176,951
[45] Date of Patent: Jan. 5, 1993

[54] REINFORCED DENTAL APPLIANCES AND PROSTHESES

[76] Inventor: David N. Rudo, 135 Madrona Pl. East, Seattle, Wash. 98112

[21] Appl. No.: 596,308

[22] Filed: Oct. 12, 1990

Related U.S. Application Data

[63] Continuation-in-part of Ser. No. 472,073, Jan. 30, 1990, abandoned.

[51] Int. Cl.$^5$ .............. A61C 13/09; B32B 27/02; B32B 33/00; B05D 3/00
[52] U.S. Cl. .................... 428/229; 156/61; 264/16; 427/491; 428/15; 428/247; 428/255; 433/169; 433/180
[58] Field of Search .............. 428/229, 247, 255

[56] References Cited

U.S. PATENT DOCUMENTS

| | | | |
|---|---|---|---|
| 3,957,067 | 5/1976 | Ferraro et al. | 132/89 |
| 4,321,042 | 3/1982 | Scheicher | 433/201 |
| 4,381,918 | 5/1983 | Ehrnford | 433/199 |
| 4,410,586 | 10/1983 | Ladizesky et al. | 428/288 |
| 4,717,341 | 1/1988 | Goldberg et al. | 433/9 |
| 4,731,020 | 3/1988 | Kawahara et al. | 433/180 |
| 4,738,622 | 4/1988 | Kawahara et al. | 433/169 |
| 4,836,226 | 6/1989 | Wolak | 132/321 |

FOREIGN PATENT DOCUMENTS

0221223A3 3/1985 European Pat. Off. .

OTHER PUBLICATIONS

*Chemical Abstracts* 107(12): 98133w.
Davis, J., "Composites, High Performance", *Encyclopedia of Chemical Technology–Third Edition*, Supplement: 260–266, 279–281 (1984).
McGarry, F. J., "Laminated and Reinforced Plastics", *Encyclopedia of Chemical Technology–Third Edition*, 13:968–978 (1981).
Frados, J. (ed.), "Reinforced Plastics", *Plastics Engineering Handbook of the Society of the Plastics Industry, Inc.–Fourth Edition*, pp. 462–466 (1976).
Kaplan, S. L. et al., "Plasma Surface Treatment of Plastics to Enhance Adhesion: An Overview", *Technical Notes*, Plasma Science, Inc., (Feb. 1990).
Kaplan, S. L. et al., "Gas Plasma Treatment of Spectra ® Fiber", *Technical Notes*, Plasma Science, Inc., (Apr. 1988).

*Primary Examiner*—James C. Cannon
*Attorney, Agent, or Firm*—Christensen, O'Connor, Johnson & Kindness

[57] ABSTRACT

A method of reinforcing a dental appliance or prosthesis comprising a resin, which includes the steps of applying to a resin portion of the dental appliance or prosthesis a lightweight, woven aramid or extended chain polyethylene fabric, and covering the fabric with more of the resin. Also disclosed are reinforcing materials (preferably a plasma-coated Spectra TM fabric), and dental appliances or prostheses reinforced by a lightweight, woven aramid or extended chain polyethylene fabric.

8 Claims, 1 Drawing Sheet

REINFORCED DENTAL APPLIANCES AND PROSTHESES

This is a continuation-in-part of U.S. Ser. No. 07/472,073, filed Jan. 30, 1990, now abandoned, the benefit of the filling date of which is hereby claimed under 35 U.S.C. § 120.

FIELD OF THE INVENTION

This invention relates generally to methods of reinforcing dental appliances and prostheses (herein collectively referred to as "dental structures"), to reinforcing materials, and to the dental structures produced by the methods. The invention also relates to the field of reinforced plastics or resins.

BACKGROUND OF THE INVENTION

Reinforced plastics are combinations of fibers and polymeric binders or matrices that form composite materials. This combination can achieve a balance of material properties that are superior to the properties of either single material. In the past, reinforced plastics have been utilized largely by aircraft, marine, automobile, and chemical manufacturers.

The combination of strong fibers and synthetic polymers to form reinforced plastics and laminates derives from several basic considerations of material science: the inherent strength of fine fibers, the wetting requirement for adhesion between the fibers and a matrix, and the ease of the liquid-solid phase change of synthetic polymers. In a general sense, the polymeric matrix serves the purpose of a supporting medium surrounding each fiber and separating it from its neighbors, and stabilizing it against bending and buckling. These functions are best fulfilled when there is good adhesion between the fibers and the matrix. Adhesion can be fostered by utilizing a relatively low-viscosity liquid polymeric precursor to impregnate a reinforcing fiber material, followed by polymerization of the matrix. Adhesion can also be enhanced by plasma surface treatment of the fibers.

Two broad categories of polymeric materials have been typically utilized to prepare reinforced resins in the prior art. These two types are the thermoplastic polymers, which generally melt in the range of 150° C. to 250° C. and readily solidify upon cooling, and the thermosetting polymers which pass through a liquid phase just once during their life, while they are being polymerized and cross-linked into heat-infusible forms.

The two predominant types of fibers that have been used to reinforce plastics, considering all uses of composites, have been glass and cellulose fibers. Fibrous glass comprises well over 90% of the fibers used in reinforced plastics because it is inexpensive to produce and possesses high-strength, high-stiffness, low specific gravity, chemical resistance, and good insulating characteristics. In reinforced plastics, glass has been used in various forms. Advantageously, it has been chopped into short lengths (6-76 mm) and gathered into a felt or matte, resulting in a form that is easy to handle and low in cost. Previously, it has been observed that the best properties in the final composite have been achieved with nonwoven fabrics in which all the fibers are straight, continuous and aligned parallel in a single direction.

In addition to glass and cellulose fibers, other types of fibers have also been used to reinforce plastic materials. The stiffest fibers known are composed of graphite, which theoretically can be almost five times more rigid than steel. However, despite much work over many years by many technical organizations, the cost of graphite fibers remains high. As a result, their use in composites is limited to applications that place a premium on weight savings: aircraft, missiles, sports equipment, etc.

In 1971, aromatic polyamide fibers became widely commercially available and are presently being used extensively in automotive tires and numerous aerospace structures. The aromatic polyamides are designated as aramids by the Federal Trade Commission, and that is the term used herein to refer to them. One specific aramid that has been widely used in many applications is referred to as Kevlar TM. Discovered in 1965, Kevlar TM is produced and marketed by DuPont.

In the stiffness range between glass and steel, aramids are lighter than glass, comparatively strong, and much tougher and absorb considerable energy before breaking, even under impact conditions. The fibers are highly crystalline and directional in character. Kevlar TM fibers are known to have excellent resistance to flame and heat, organic solvents, fuels and lubricants, and they can be woven into fabric. Because of their strength and other properties, aramid fibers have been used in sports equipment, and in protective systems where ballistic stopping exploits their superior impact resistance.

More recently, fibers of ultra-high strength polyethylene have been produced. Such fibers are available from Allied Signal, Inc., Fibers Division, Petersburg, Va., under the trademark Spectra TM, and Dutch State Mining Corporation. The fibers are made of extended chain polyethylene and have a low specific gravity of about 0.97, which is less than the specific gravity of fiberglass or aramid fibers.

Although composites have been used in the past in a number of settings, their use has not been fully exploited in all fields. The present invention involves the use of a lightweight woven fabric, such as an aramid (e.g. Kevlar TM) or a polyethylene (e.g. Spectra TM) to reinforce resinous portions of dental structures, such as dental prostheses and other restorative appliances. Previously, the possibility of using a lightweight woven fabric in synthetic resinous portions of dental structures has not been reported.

The following publications exemplify prior uses of aramids in the context of dental applications:

European Patent Application No. 0,221,223 discloses a magnetic retaining device for dental prostheses, comprising magnets intended to be implanted in the upper or lower jawbone within casings of a biocompatible material, and corresponding elements incorporated in the prosthesis which are magnetically attractable by the implanted magnets. According to this European patent application, the prostheses can be rendered lighter by forming the prostheses from a hollow body of resin which carries the teeth, the cavity of which is filled with a mass of composite material of resin and reinforcing fibers, normally glass fibers or Kevlar TM. It is likely that in the context of the prior art, those working in the dental field would likely have selected relatively short fibers of glass or Kevlar TM for the reinforcement purposes described in this European patent application.

On the other hand, as discussed in greater detail hereinbelow, the present invention relates to the use of a woven fabric of an aramid (such as Kevlar TM) or of a polyethylene (such as Spectra TM) to reinforce resinous portions of dental prostheses and dental appliances, and to particular methods tailored to producing such reinforced resin-containing dental structures.

Kawahara et al., U.S. Pat. No. 4,731,020 discloses a removable denture retaining structure which is mounted on an elastic member that is located between the denture body and a support base. The patent further discloses that the elastic support member may be reinforced with a wide variety of organic fibers, ceramic fibers, glass fibers, etc. However, this patent does not relate to reinforcement of the dental prosthesis or appliance itself, as with the present invention. Moreover, the resins to be reinforced in accordance with the present invention are preferably nonelastomeric, in direct contrast to the elastomeric mounting member of Kawahara et al.

Kawahara et al., U.S. Pat. No. 4,738,622, contains essentially the same disclosure as Kawahara et al., discussed above.

Goldberg et al., U.S. Pat. No. 4,717,341, is directed to an orthodontic appliance system, the components of which are formed from fiber reinforced composite material comprising a polymeric matrix, and at least 5% of a reinforcing fiber embedded in the matrix. The patent states that although a variety of fibers may be employed, the most commonly utilized fibers are glass, carbon and/or graphite and aramid fibers (referred to in the patent as polyaramid fibers). In contrast to the present invention, the thrust of the Goldberg et al. patent, and all of the examples therein, relate to the use of unwoven fibers (especially glass, but also "aramid") to reinforce appliances, rather than woven fabrics.

Also, the Goldberg patent relates to reinforcement of the force-imparting portions of orthodontic appliances: primarily wires, but also including arches, segments, hooks, tie-backs, ligature wires and springs, pins, brackets, tubes, active lingual appliances, etc. These appliances are designed and configured to exert active force on a natural oral structure such as a tooth. The reinforcement of the dental prostheses and appliances of the present invention involves non-force-imparting portions thereof. It should be noted that woven fabric reinforcements are incompatible with wires and springs.

Ferraro et al., U.S. Pat. No. 3,957,067, and Wolak, U.S. Pat. No. 4,836,226, are each directed to dental floss or dental floss-like articles in which one of the materials that could be used to make the article is Kevlar TM. Neither of these patents is directed to reinforced resins, and they are cited herein only because they disclose another use of Kevlar TM in a dental setting.

In spite of the above-described prior art, a number of possible types and applications of composite resins in the dental field have not been described or suggested.

It is therefore an object of the present invention to provide reinforced dental structures which include at least a portion made of a resinous material.

It is yet another object of the present invention to provide a method for reinforcing resin-containing dental structures.

Another object of the present invention is to provide a reinforcing material having superior bonding and strength-imparting properties.

SUMMARY OF THE INVENTION

In accordance with the present invention, the above-noted objects, and others that will become more apparent hereinafter, have been fulfilled by the discovery that synthetic resin containing dental structures can be reinforced by combining therewith a lightweight woven fabric comprising aramid or polyethylene fibers.

The method of the present invention will generally involve applying one or more layers of a lightweight woven fabric to a dental structure to be reinforced, and typically covering the fabric with more resin, so that in the final dental structure the fabric is not exposed. The process will be tailored to the particular type of resin and to the particular type of dental structure to be reinforced.

DETAILED DESCRIPTION OF THE PREFERRED EMBODIMENTS

Figure 1:
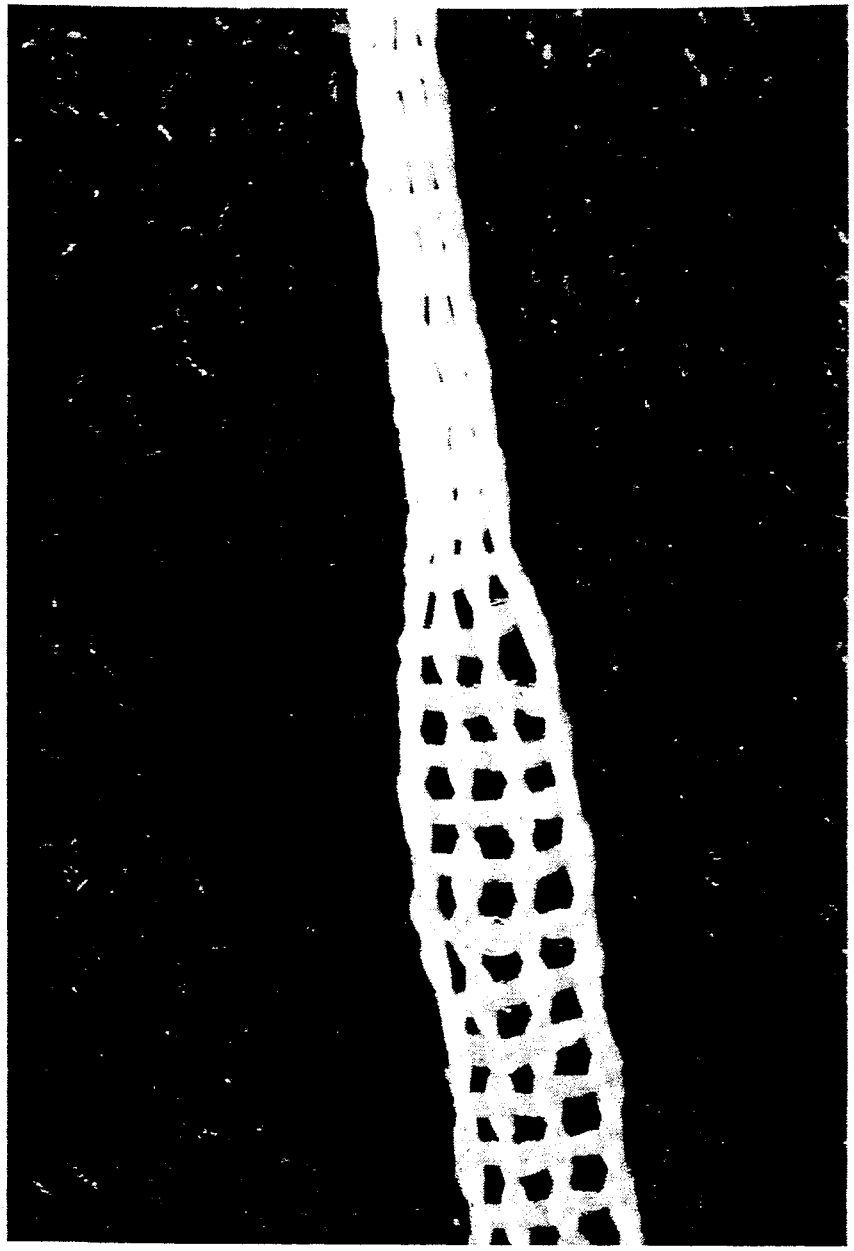
FIG. 1 depicts plasma-treated Spectra TM fibers woven in a leno weave, which could be used for reinforcement purposes in accordance with the present invention.

One aspect of the present invention relates generally to a method of reinforcing a resin portion of a dental structure, which comprises the steps of applying one or more layers of a lightweight woven fabric made up of polyaramide or polyethylene fibers to a resin portion of a dental structure, and covering the woven fabric with more of the resin.

The woven fabric of the present invention preferably comprises an aramid polymer or a high-strength, extended chain polyethylene. Aramid fibers are well known to those of skill in the art and are commercially available from, for example, Dupont. Dupont's aramid fibers are marketed under the trade name Kevlar TM. Kevlar TM is the preferred aramid of the present invention. Chemically, Kevlar TM fibers are poly(p-phenyleneterephthalamide). Three grades of Kevlar TM fibers are produced by Dupont: Kevlar TM, which is made specifically for reinforcing rubber; Kevlar TM 29, made primarily for use in ropes, ballistics, etc.; and Kevlar TM 49, made for reinforcing plastics in aircraft, aerospace, marine and sporting goods applications. For the purposes of the present invention, the woven fabric will preferably be formed from fibers of Kevlar TM 29 or Kevlar TM 49. It should be understood, however, that the inventor contemplates the use of other aramids besides the preferred embodiment, Kevlar TM, as long as the aramid has suitable properties, such as strength and the ability to be woven.

The high-strength polyethylene fibers are made up of extended chain polyethylene having a tensile strength of about $375.0 \times 10^3$ to $435.0 \times 10^3$ psi.

An important aspect of the fabrics is their weight. The weight of a fabric, as well as its fineness, may be reported in terms of its "denier". As is known in the textile art, a denier is a unit of fineness based on a standard of 50 milligrams per 450 meters of yarn. The fabrics of this invention are lightweight, i.e., for the aramids, they preferably have a denier of less than 100, e.g., about 50 to about 75. The preferred aramid fabric is a Kevlar TM 55 denier cloth. For the polyethylenes, the fabrics preferably have a denier of 215 or less. One specific polyethylene fabric is a Spectra TM 185 denier cloth.

The fabric may be cut from a bolt of cloth or preferably from a ribbon, for example. A ribbon is the particular preferred form of plasma-coated Spectra TM having a leno weave. By "ribbon" is meant a narrow and long piece of fabric, which when cut in the width direction will not result in substantial unravelling of the leno weave. Typically the length: width ratio for such ribbons will range from 50:1 to 5000:1, preferably 250:1 to 2500:1. To facilitate cutting loosely woven fabric, especially Kevlar ™, cloth, an adhesive-backed tape such as 3M Post-It ™ tape can be placed on both sides of the cloth and the desired shape and size obtained by cutting the cloth.

To remove the tape, it can be soaked in the liquid monomer of the resin. Preferably, the cloth should be rinsed a second time with clean monomer before it is used to reinforce a dental structure.

The fabric is woven from individual threads made up of multiple filaments twisted together. The fabrics may be of varying thickness and with tight or loose weaves, depending upon the application. The preferred weave of fabric has about a 30×30 to 80×80 construction. The weaving may be any type, such as a balanced weave containing equal amounts of fibers or filaments in each direction, or a unidirectional weave, with more fibers running in one direction than another. The fabric can be used as is, or it may be provided and used in a form that is already impregnated with resin, i.e., a prepreg. The fabric may also be treated with sizes, finishes, such as a plasma treatment, and the like, to promote maximum adhesion by the resin.

A particularly preferred reinforcing material is made up of high-strength, extended chain polyethylene, preferably Spectra ™, which is woven in a so-called leno weave. A leno weave is shown in FIG. 1 herein. Leno weaves are lightweight and open, giving a lace-like appearance. Because of this, the fabric can take any shape and interlock easily with the matrix material. Leno weaves are made by twisting adjacent warp yarns around each other, then passing the filling yarn through the twisted warps.

The following U.S. patents, which are hereby incorporated by reference in their entirety herein, contain disclosures involving inter alia leno weaves and their properties: U.S. Pat. Nos. 4,665,951; 4,960,349; 4,944,987; and 4,816,028.

Spectra ™ is preferably produced in the form of a plasma surface-treated leno woven ribbon for the uses described herein. The ribbon can best be cut using a sharp blade. The ribbon should not be touched by bare skin but only with cotton or rubber gloves so as not to contaminate the plasma-treated surface, which could reduce its ability to adhere to the matrix material. It is known that gas plasma treatment of Spectra ™ fiber can result in epoxy composites which possess outstanding properties. Such fibers may be used in accordance with this invention. Preferably, cold gas plasma is utilized to treat Spectra ™ fiber. The primary objective of this gas plasma treatment is surface modification, wherein hydrogen atoms are abstracted and replaced with polar groups (e.g., hydroxyl, carboxyl, carboxy, and the like). The presence of polar or functional chemical groups on the surface of the fiber enhances wetability by and reactivity with a resin matrix, thus promoting excellent adhesion between the fiber and the matrix.

Multiple layers of thinner fabric are stronger than a single layer of a thicker fabric. When using the fabric in layers as a laminate, the multiple layers act like a box beam which resists flexing and bending. Single as well as multiple layers of fabric are contemplated in connection with the present invention. Regarding the use of multiple layers, for example, two to five layers of lightweight fabric may be advantageously employed.

Fabric reinforcement is also stronger when the threads of different layers of fabric do not run parallel with respect to each other. For example, neighboring layers can be set such that some of the threads from neighboring layers will form a 45° angle relative to each other. More generally, angles of from 15°–60° could also advantageously be employed.

Since the cloth may not not polish well, it should usually be covered on the surface with more resin material. While the resinous covering will generally be the same resin as the underlying reinforced resin layer, a different resinous covering could also be employed, as long as it exhibits sufficient adhesion both to the cloth and to the underlying resin that has been reinforced. For some applications, a portion of the fabric may be exposed, if necessary or desirable.

To prepare the woven fabric for use, the first step will be to cut the woven fabric to the desired size and shape, if necessary. Since the fabric will act like a sponge, absorbing liquid synthetic material that is being used, the cloth should generally be soaked in a thinning agent before it is laminated with the synthetic material. For example, before using an acrylic resin, the fabric should be soaked in the acrylic acid monomer, which serves as the thinning agent. When using with a composite material, the fabric should first be wetted with an unfilled liquid.

The specific nature of the polymeric matrix (i.e., the resinous portion) is relatively unimportant for the purposes of the present invention. The basic requirements of the polymeric material are that it be compatible with a particular dental use and capable of sufficiently adhering to the woven cloth to result in a suitably reinforced material. For example, the polymeric materials employed as the matrix for the reinforcing fabric may be thermoplastic or thermosetting materials, or composites of various types.

The polymeric materials are generally nonelastomeric. An "elastomer" is defined as a material which at room temperature can be stretched under low stress to at least twice its original length and, upon immediate release of the stress, will return with force to its approximate original length. For example, elastomeric polyurethane rubber material is typically not a suitable resin for the present purposes.

The polymeric material of the present invention may include polyesters, epoxy resins, and various thermoplastic materials. Thermoplastic materials include nylon, polystyrene, polyethylene, polypropylene, styrene/acrylonitrile, polycarbonate, and polysulfone. Generally, the resin will be one that is synthetically prepared. Preferably, the resin is an acrylic resin, such as bis-GMA resin, which is a standard resin familiar to dentists.

The amount of cloth used to reinforce a particular dental structure will depend upon the reason for the reinforcement and, hence, the size of the area desired to be reinforced. Based on the conventional understanding and experience of those working in the field of dentistry it will typically be possible to predict in advance which portions of a given dental structure will need reinforcement.

It should also be noted that the larger the area included with the cloth reinforcement, the stronger it will be. Therefore, one of ordinary skill in the art will be able to tailor the strength of a particular dental structure by adding more or less of the woven fabric material to the resinous portion of the structure. In general, the amount of the fabric relative to the amount of resin, in volume percent, will be at least about 5%, up to about 50%.

The types of dental structures that can be reinforced are varied. Generally, the present invention is directed to reinforcement of non-force-imparting portions of dental structures that include as a part thereof a resinous portion. By non-force-imparting is meant that the resinous portion does not substantially actively (i.e., constantly) press or pull any oral structure, such as a tooth. That is, the resinous portion to be reinforced in accordance with this invention, is one that is present for positioning the dental structure or to substitute for a natural oral structure. For example, whereas a wire, spring or bracket used for orthodontic purposes is not within the scope of "non-force-imparting dental structures", a resinous portion for positioning an orthodontic retainer is. Specific examples include complete resinous portions of dentures, removable partial dentures, temporary removable bridges, provisional fixed bridges, crowns made of synthetic materials, and materials used to splint teeth together, etc. The cloth is used in accordance with the present invention to reinforce the resinous portion of the dental structure itself, rather than to reinforce a mounting element for the dental structure. The fabric-reinforced laminate can also be used to maintain dimensional and positional stability in making implant impressions.

The process for reinforcing the dental structure will vary depending upon the type of resin and dental structure being reinforced. A brief outline of some specific types of procedures is provided below:

1. Using a heat cured resin (e.g., a thermosetting resin) with a trial packing method.
   A. Pack and trial pack the flasked appliance in the standard manner.
   B. Remove most of the resin in the area to be reinforced, leaving just enough to cover the model so that the cloth does not touch the model.
   C. Lay on one or more layers of the lightweight woven fabric covering as much area as possible.
   D. Cover fabric with more resin and trial pack until flask is fully closed.
2. Using a cold self-curing resin (e.g., a thermoplastic resin).
   A. Place a thin layer of self-curing resin on the model.
   B. Push one or more layers of woven fabric down into the resin, but not touching the model with the fabric.
   C. Layer more resin over the fabric.
   D. Carry out finishing in the standard manner. Feel free to cut through areas of fabric in the final shaping of the case. Where fabric is exposed on the surface, it should be covered with a thin coat of resin and polish.
3. Using chemically-activated composite: reinforce in the same manner as a self-curing resin.
4. Using light-activated composite.
   A. Place a very thin layer of composite on the model and cure it with light.
   B. Place a layer of woven fabric over the initial layer of composite and wet it with unfilled composite making sure there are no air pockets between the layers. Cure with light longer than normally done (e.g., about 1.5–3 times, preferably 2 times the normal time). The cloth is substantially opaque and therefore inhibits the transmission of light through it. A laboratory light works best.
   C. (Optional) Apply more layers of cloth for added strength in the same manner as the previous step.
   D. Cover last layer with filled composite and cure.
   E. Finish the appliance in the standard manner. Feel free to cut through the fabric in the final shaping of the case. Where fabric is exposed on the surface, cover with a thin layer of composite and polish.
5. For use in repairing removable prostheses or appliances.
   A. Prepare the case for repair using the standard procedure for making a stone or plaster matrix.
   B. If the case can be removed from the plaster matrix, cut back the area to be repaired a few millimeters (e.g., about 1–4) from the fault and place it back on the plaster matrix. If the case cannot be removed from the matrix, remove enough material so as to have the thinnest amount of original material possible at the fault.
   C. Remove as much original material as possible over a large area. The greater the area covered with the cloth, the stronger will be the repair. Wet the surface with the liquid used for the repair and complete the repair in the same manner previously stated for the construction of new appliances and prostheses.
6(a). For strengthening provisional fixed prostheses made of resin.
   A. The provisional prosthesis is made in the standard manner and the occlusion is adjusted.
   B. A deep, wide channel is cut through the entire occlusal surface including over the abutment teeth.
   C. A length of cloth (i.e., fabric) is cut to fill the entire length of the channel. The cloth is rolled and packed into the channel. Alternatively, the cloth is pulled apart to open spaces created by the weave without rolling, thereby facilitating and improving adherence of the cloth to the surrounding matrix. The greater the mass of cloth, the stronger the provisional prosthesis.
   D. The cloth is soaked with monomer. Excess monomer is blotted or blown off and a thin mix of resin is worked into the cloth in the channel saturating the cloth with resin.
   E. The case is finished. If cloth touches the surface, it can be cut back and more resin added to provide a surface of resin.
6(b). Another method of constructing a provisional prosthesis made of resin or composite.
   A. Place a layer of light-cured resin or unfilled composite (i.e., matrix material) over a crown or bridge abutment on a model and cure in the standard manner.
   B. Adhere the cloth (preferably in ribbon form) to the first layer, using more of the uncured resin or unfilled composite.
   C. Position the cloth in the shape that is desired, cover it using more of the matrix material, and cure (e.g., by exposure to light).
   D. Complete the provisional prosthesis in the standard manner.
7. For repairing or strengthening provisional fixed prostheses using chemically-cured composite, use the same technique as with resin in general except soak the cloth with an unfilled composite and add a filled composite over it.
8. For strengthening or repairing provisional fixed prostheses using light-cured composite, the same technique as using resin in general is followed until the stage where the cloth is used. Instead of using a roll of cloth, use layers of cloth and proceed in the same manner as previously outlined in the construction of a prosthesis using light-cured composite. If the cloth is exposed on the occlusal surface, it can be trimmed back and covered with a layer of filled composite.

9. Method of splinting teeth together.
   A. Acid etch and bond a layer of light-cured resin or unfilled composite (i.e., matrix material) to teeth.
   B. Adhere cloth to first layer, using the same matrix material.
   C. Cover the cloth with acrylic or additional composite.

On provisional fixed prostheses made using any of the above methods, the occlusal surface would be more resistant to wear if the surface was reinforced with cloth such as Kevlar TM, or more preferably, plasma-coated Spectra TM in a leno weave.

It will be appreciated that various modifications can be made based on the above disclosure without departing from the spirit and scope of the present invention.

The embodiments of the invention in which an exclusive property or privilege is claimed are defined as follows:

1. A plasma-treated woven polyethylene fabric ribbon, wherein said fabric is woven in a leno weave.

2. A fabric according to claim 1, wherein said plasma treatment is carried out in a cold gas plasma which replaces hydrogen atoms on the surface of high strength extended chain polyethylene fibers with polar groups thereby promoting adherence between said fibers and a non-elastomeric polymeric matrix.

3. The fabric ribbon of claim 1 having a denier of 215 or less.

4. The fabric ribbon of claim 1 having a length to width ratio of 50:1 to 5,000:1.

5. A material for reinforcing a dental appliance or prostheses, the material comprising a plasma-treated woven polyethylene fabric ribbon, wherein said fabric is woven in a leno weave and embedded in a resin matrix.

6. The material of claim 5, wherein said plasma treatment is carried out in a cold gas plasma which replaces hydrogen atoms on the surface of high strength extended chain polyethylene fibers with polar groups thereby promoting adherence between the fibers and a non-elastomeric polymeric matrix.

7. The material of claim 5, wherein the fabric ribbon has a denier of 215 or less.

8. The material of claim 5, wherein the fabric ribbon has a length to width ratio of 50:1 to 5,000:1.

* * * * *